United States Patent [19]

Braiman

[11] Patent Number: 5,346,397
[45] Date of Patent: Sep. 13, 1994

[54] PROCESS FOR MAKING CERAMIC DENTAL CROWNS

[76] Inventor: Kenneth S. Braiman, 6723 La Loma Dr., Jacksonville, Fla. 32217

[21] Appl. No.: 76,981

[22] Filed: Jun. 15, 1993

[51] Int. Cl.$^5$ .............................................. A61C 5/10
[52] U.S. Cl. .................... 433/223; 433/202.1; 433/212.1; 433/218; 264/19
[58] Field of Search ................ 433/202.1, 212.1, 218, 433/222.1, 223; 264/19, 20

[56] References Cited

U.S. PATENT DOCUMENTS

| | | | |
|---|---|---|---|
| 4,556,389 | 12/1985 | Ueno et al. | 433/223 |
| 4,810,193 | 3/1989 | Wieder | 433/26 |
| 5,192,207 | 3/1993 | Rosellini | 433/223 |

*Primary Examiner*—John J. Wilson
*Attorney, Agent, or Firm*—Arthur G. Yeager

[57] ABSTRACT

A process for making artificial porcelain teeth or laboratory fabricated dental crowns includes casting or molding a plurality of tooth-shaped unfired shells from ceramic powder and a resin, acrylic, wax or starch in liquid form and molded and hardened into shapes of predetermined tooth contours. These dried powder like, thin and highly characterized outside shells of a general tooth shape are then merged into a full porcelain powder buildup of the tooth shape by using conventional porcelain powders mixed into a paste, conventionally, as a filling medium completing the buildup of tooth or crown form. This form is then placed into a furnace and heated to purge undesired resin, acrylic, wax or starch and other extraneous material, and then it is baked conventionally to further purge same and obtain an artificial tooth or crown in the most desirable form possible for the technician who then finalizes the contour by grinding and polishing or glazing same conventionally. The powder like dried shell may be used with a substructure or glass core or refractory die. The process preferably includes the provision of determining the proper color of porcelain powders to use to arrive at the final color of the tooth or crown even before firing and baking the shell and filling medium.

11 Claims, 2 Drawing Sheets

PROCESS FOR MAKING CERAMIC DENTAL CROWNS

BACKGROUND OF THE INVENTION

The fabrication of teeth for ceramic crowns, bridges or implants, has always been a time-consuming, expensive process. A technician must prepare a pasty mixture of a ceramic powder and a liquid which gradually dries into a packed powder. While it is drying the technician must mold and carve the pasty mixture into a shape resembling the natural tooth it is replacing, or in the case of an all ceramic crown, also match the contours of the tooth stump to which it is to be affixed. Not only is the shaping operation time consuming and difficult, but there is also the problem of the proper blending of colors in order to match the color of the teeth to each other and/or to those natural teeth adjacent to the one being fabricated.

This invention provides a process for making a plurality of generic tooth-shaped thin enamel-like shells of the various types of teeth found in various persons which can then be filled and carved to a final shape and tinted to a final color with an enormous savings in time of technician's labor and cost of the finished tooth or crown which is also less dependent on the sculptural and artistic skill level of the technician.

It is an object of this invention to provide a novel and efficient process for making an artificial tooth or dental crown. It is another object of this invention to provide a novel process for preparing a tooth enamel shell which is then filled with colored dentine material to arrive more precisely to the final product in color and shape. Still other objects will appear from the more detailed description which follows.

BRIEF SUMMARY OF THE INVENTION

This invention relates to a process for fabricating an artificial tooth or dental crown which comprises selecting a prefabricated solid thin tooth-shaped enamel shell molded from a hardenable liquid mixture of acrylic powder and ceramic powder, or resin and ceramic powder, or heated waxes and ceramic powder, or watered starch and ceramic powder most nearly resembling the facial contours of the tooth or crown desired according to an impression taken by the dentist of a patient, and subsequently filling under this outer surface with a paste of colored porcelain powders, purging the two together by heating to purge or to remove extraneous material from the shell, baking the fired tooth or crown, grinding same, and polishing or glazing same to achieve the final tooth or crown.

In specific embodiments the shells may be attached to a concave metal understructure, which, in turn, is attachable to a prosthesis support in a patient's mouth.

DETAILED DESCRIPTION OF THE INVENTION

Figure 1:
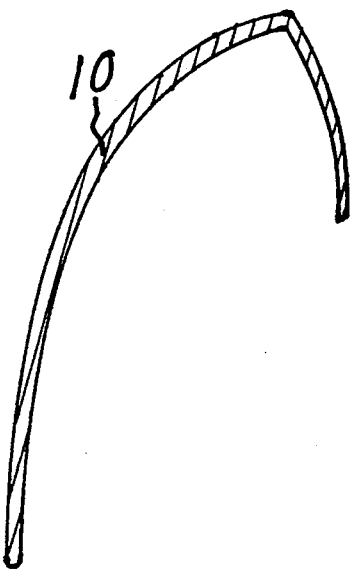
FIG. 1 is a cross-sectional view of the dried, powder like, thin outside shell for an incisal crown fabricated in accord with this invention.
Figure 2:
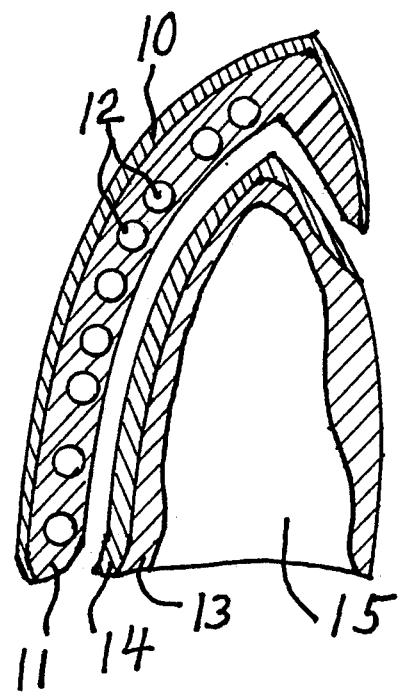
FIG. 2 is a cross-sectional view of shell of FIG. 1 after filling with the porcelain powder paste and porcelain beads and exploded therefrom is the metal substructure with the opaque porcelain material applied thereof.
Figure 3:
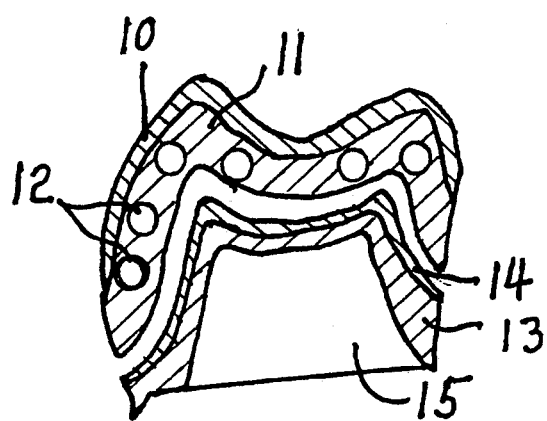
FIG. 3 is a cross-sectional view similar to FIG. 2 and showing a molar crown.
Figure 4:
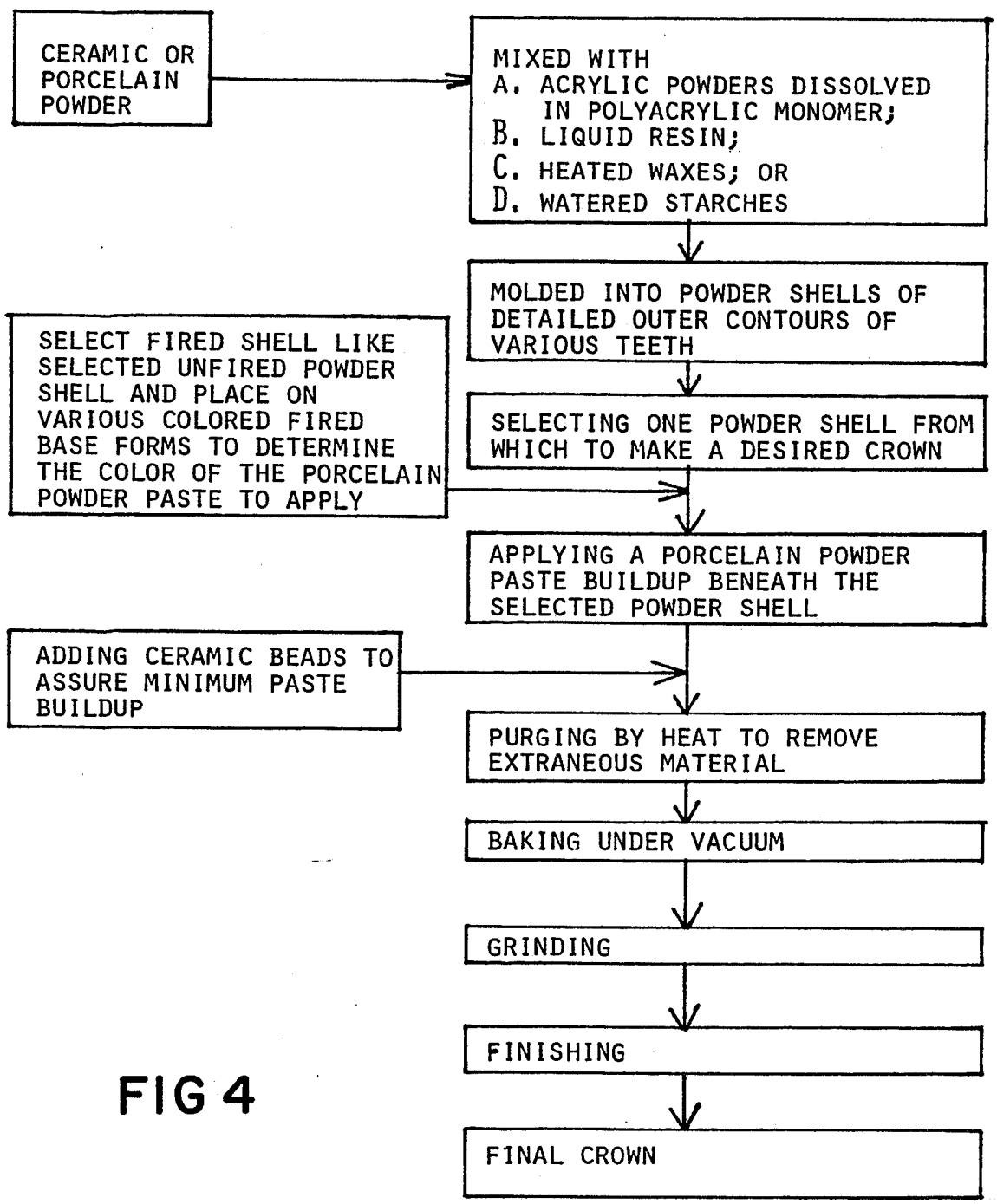
FIG. 4 is a diagrammatic view of the process for making a dental crown in accord with this invention.

The process of this invention begins with the selection of a powder like, unfired tooth blank or shell from a supply of prefabricated or premolded generic blanks or shells including incisal shell 10 depicted in FIGS. 1 and 2 or molar shell 10 depicted in FIG. 3. Such blanks or shells are premolded teeth or crowns which are contoured in the mold to resemble no particular person's tooth, but merely to resemble a molar, an incisor, or a bicuspid in many different styles and sizes. Subsequent contouring and filling and colorizing may be done in the build-up stage to make the blank or shell match as exactly as feasible the tooth being replaced or repaired in the mouth of the particular individual involved. The powder blank of shell is prepared by (1) providing a moldable mixture or porcelain powder and a predetermined small amount of polymeric resin powder, (2) dissolving those powders in a monomeric material which will polymerize and harden, and (3) pouring the mixture and material into molds for teeth and allowing the solution to polymerize and harden into a rigid powder shell and a specific thickness, graduating from thick at the occlusal or incisal, to a very thin zone at the gingival.

The molded powder blank or shell 10 must be filled by a paste 11 of conventional porcelain powders of various colors and then fired or purged to remove any extraneous organic materials. These may be portions of the mold, residue from any mold release agent employed, all acrylic matrix material, portions of the molding materials, etc. After this purging to burn off the undesirables, the filled blank or shell 10, 11 is baked in a conventional manner and then subjected to grinding, polishing or glazing in a conventional manner. The contoured blank has been subjected to high temperature firing in a vacuum furnace and is ready to be sent to the dentist. The paste 11 of conventional porcelain powders will include coloring matter to achieve the final color desired.

The invention also includes the prediction of the final color of the processed or fired tooth or crown prior to firing thereof. A plurality of color swatches are made and fired and baked with varying colors conforming to normal colorations of teeth.

A selected series of the generic tooth-shaped thin powder enamel shells are fired without filling, etc., in an oven and baked to provide semi-clear glass-like enamel shells. A series of different colored base swatches are also prepared to represent the inner dentine layer, which has various dentine hues and croma that blend with the enamel shells to make a specific color, the technician who chooses the color of the dentine based material may select any body colored swatch and combine it with one of the various intensities of semi-clear glass-like fired enamel shells to perceive what the final resulting crown will end up looking like. The related swatch and semi-clear glass-like enamel shell are combined temporarily by the use of an interlayer of glycerin which allows the two different colored materials to blend together into one perceived color. Once the proper combination is chosen a corresponding unfired powder shell is selected and is filled and colored by the appropriate paste of conventional porcelain powders matching the swatch indicating the proper mixture and blend to the technician. Thus a coloring layer of dentine porcelain is applied under the unfired powder shell to ultimately obtain the same tint as that of the referenced fired and baked swatch and shell. The colorant layer is typical to a conventional dentine layer of porcelain with various ceramic powders using appropriate small amounts of dyes or pigments to provide the appropriate yellowish, tannish, or grayish color. As soon as the proper color of swatch is determine, the appropriate and corresponding base or dentine paste is applied to the unfired powder shell and the colored paste build up is purged in a furnace and subsequently baked to fix the color permanently. Following the above steps the grinding, and polishing or glazing is applied in a conventional manner.

The coloring paste or dentine porcelain is applied to the unfired generic blank or shell, which becomes the enamel layer, as a thick, viscous liquid, preferably by use of a brush or a spatula. It is important to apply a sufficient amount of dentine porcelain powders under the unfired powder generic shell to provide an unvarying color to the entire tooth or crown being produced. Dentinal layers are generally about 0.5 mm–1.5 mm thick, but must be at least 0.5 mm. A method for assuring that the minimum thickness under the powder shell is achieved, is to incorporate into the coloring paste or dentine porcelain layer, a plurality of small ceramic beads 12 of 0.5 mm in diameter. The beads will keep the dentine porcelain layer from ever compressing to less than the minimum needed, simply by their physical presence. The color is unsatisfactory only if the layer is too thin; thicker layers will have the desired color. Enamel layers may be applied on top of or over the shell to further customize the crowns contour, simply by adding the conventional enamel paste with a brush or spatula in a conventional manner. After all paste is applied to the selected unfired powder shell it is purged to remove extraneous material, including resin or acrylic therefrom in an oven at about 600 degrees F.–1200 degrees F. for a time period of 2 to 15 minutes. After purging the blank or shell is baked in a furnace under vacuum conventionally at temperatures starting at about 1000 degrees F. and rising to approximately 1700 degrees F. in a time period of 5 to 20 minutes which further purges same. Grinding and polishing or glazing may also be undertaken in a conventional manner on the fired shell to provide the final tooth or crown.

In some instances, particularly in the case of crowns, the blank or powder shell may be originally attached to a metal understructure 13 by the dentine ceramic opaque paste 14 which bonds to the understructure typical to conventional methods.. The understructure has a concave recess 15 to fit over whatever stump is on the tooth to be crowned.

The ingredients of the material to be molded generally include ceramic powder, a small amount of polymeric powder, and a monomer. The ceramic powder may be powdered porcelain or its equivalent. The polymeric powder may be any of several materials, e.g., polyolefin, polyester, polyamide, polyacetal, polyvinylhalide, or the like, but the preferred material is a polyacrylic, such as polymethylmethacrylate, polyacrylamide, polyethylacrylate, etc. The monomer is a partially polymerized polymethylmethacrylate in the form of a thick syrup. A catalyst can be employed to cause the monomer to polymerize and harden when exposed to light. These photo-initiating catalysts are well known in the industry, e.g., peroxides. Also the powder shells may be made from liquid and hardenable mixtures of ceramic powders with resins, waxes or starches.

Among the advantages of the present invention, the most important is that the dental technician can start with a prefabricated highly contoured powder tooth blank or shell rather than starting from an unmolded glob of putty-like material. These blanks or powder shells are prefabricated in different tooth styles, sizes and contoured shapes, so as to minimize the work and talent of the dental technician to prepare the first phase and the buildup phase of a tooth or crown. Another important feature is the provision of sample coloring combinations of a dentin-colored and fired tooth swatch and an outer fired enamel shell. With several such combinations in hand the dental technician is guided directly to the exact material needed to obtain the shade desired for the coloring layer or dentine to be, and the amount of tint of the dentine porcelain powders to be employed in applying the paste to the unfired powder blank or shell. A good and predictable result can thus be achieved without undergoing several buildups and firings before finding the desired combination. Without the benefit of this type of color build-up, the technician is forced to guess at amounts and tints of each layer, including the time and expense of firing each combination; and to renew the procedure several times until a successful trial produces the desired color in the final result.

In summary the preferred method includes employing mixtures of acrylic powders with the ceramic powders in the molding of the powder blanks or shells 10. Such powders are dissolved in a polymerized polyacrylic monomer to provide a first phase result of an unfired porcelain powder shell of tooth or crown which has a great amount of highly detailed anatomical contours and durability prior to being fired. The technician then determines the color by instructions from the dentist or he can reasonably ascertain the final color by trying various colored and fired bases releasably attached to a fired semi-clear form of glass to the one chosen. The aforementioned tooth-shaped shells or partial shells are fired in a porcelain furnace without any addition of extra porcelain powders to obtain semiclear shells of glass duplicating the outer surface of a finished and completed crown. These glass like forms will be placed on a number of different colored fixed base forms that precisely match the inside shape of the semi-clear glass forms so that when placed together they appear to be one piece. By interchanging these different colored and fired base forms with the use of a glycerin as filler and a partial adherent between the selected colored base form and the fired semiclear glass forms one can observe the ultimate shade of a fully processed tooth or crown can be determined without performing the processing procedure with each of these different base colors, thus saving an enormous amount of time and material. When the proper color is determined, a specific mixture of porcelain powders is indicated by the appropriate colored base and the technician uses that mixture to fill under the appropriate unfired tooth or crown shell selected prior to firing same. Beads 12 of a predetermined size and corresponding dentine color may be employed in the mixture to assure a proper thickness thereof between the outer shell and the matrix surfaces of the final crown, i.e., metal substructure, glass core, or refractory die.

While the invention has been described with respect to certain specific embodiments it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A process for making a ceramic dental crown comprising the steps of:
   A. molding approximate tooth-shaped unfired thin powder shells representative of various teeth from a hardenable liquid mixture of ceramic powder and a predetermined small amount of at least one member of the group consisting of
      i) acrylic powders dissolved in a polyacrylic monomer,
      ii) liquid resin
      iii) heated waxes
      iv) watered starches into shapes of a generally sturdy matrix having approximate predetermined tooth shapes and having highly detailed anatomical contours of various teeth;
   B. selecting one of the unfired powder shells of approximate predetermined tooth contours having the greatest similarities to the crown desired for a particular patient;
   C. applying a paste buildup of conventional porcelain powders to the selected one of the unfired powder shells to fill same into a more detailed fit molding to a conventional substructure;
   D. purging the selected paste buildup and one powder shell by heating same which purges extraneous material therefrom;
   E. baking the purged selected one buildup and shell under vacuum in a conventional manner to eliminate one member of the group in step A and obtain a solid homogenous ceramic crown;
   F. grinding the baked crown to its final shape in a conventional manner; and
   G. finishing the ground baked crown to its final shape and appearance in a conventional manner to produce the final ceramic crown.

2. The process of claim 1 wherein step D is performed at about 600 degrees–1200 degrees F. for a time period of 2–15 minutes.

3. The process of claim 1 further comprising the steps of:
   H) selecting a fired form of a tooth-shaped thin shell substantially identical to the unfired selected one of the shells in step B;
   I) placing the selected fired form onto a number of different colored fired base forms which are complemental with and fit onto the selected fired form with the use of a clear filler therebetween;
   J) determining the proper color from one of the colored fired base forms of the paste to be applied in step C under the tooth-shaped thin shell selected in step A.

4. The process of claim 3 wherein glycerin is the clear filler in step I.

5. The process of claim 1 wherein step C includes the step of adding a plurality of predetermined sized ceramic beads which are covered by the paste build up to assure sufficient amount of properly colored paste build up being applied beneath the selected one of the shells.

6. A process for making a ceramic dental crown from a plurality of molded approximate tooth-shaped thin unfired but rigid ceramic powder shells having detailed anatomical contours representative of various teeth comprising the steps of:
   A. selecting from the plurality of molded thin shells containing ceramic powders one having the size and shape and desired enamel color according to the crown desired of a particular patient according to an impression made by the dentist;
   B. applying a paste buildup of conventional porcelain powders under the selected one of the thin powder shells to fill same into a more detailed fit matching the prep form from the impression made by the dentist;
   C. firing the selected paste buildup and one powder shell with filler dentine therein to remove extraneous material therefrom;
   D. baking the fired one shell under vacuum in a conventional manner to obtain a baked ceramic crown;
   E. grinding the baked crown to its final shape in a conventional manner; and
   F. polishing or glazing the final shaped tooth or crown in a conventional manner to obtain the ceramic crown to be sent to the dentist.

7. The process of claim 6 wherein the plurality of molded thin powder shells containing ceramic powders are castings prepared from a hardenable liquid mixture of the ceramic powders and a predetermined small amount of at least one member from the group consisting of:
   i) acrylic powders dissolved in a polyacrylic monomer,
   ii) liquid resin
   iii) heated waxes
   iv) watered starches.

8. The process of claim 6 wherein step C is performed at about 600 degrees–1200 degrees F. for a time period of 2–15 minutes.

9. The process of claim 6 further comprising the steps of:
   G) selecting a fired form of a tooth-shaped thin shell substantially identical to the selected one of the unfired shells in step A;
   H) placing the selected fired form onto a number of different colored fired base forms which are complemental with and fits onto the selected fired form with the use of a clear filler therebetween;
   I) determining the proper color from one of the colored base forms of the paste to be applied in step B to the selected one thin shell from step A.

10. The process of claim 9 wherein step H includes applying glycerin as the clear filler between the selected fired form and the colored fixed base form to blend into one perceived color that can be predictably duplicated if fired together.

11. The process of making ceramic dental crowns comprising the steps of:
   A. fabricating various crown shapes and sizes;
   B. preparing a liquid hardenable mixture of ceramic powders and a predetermined small amount of at least one member from the group consisting of:
      i) acrylic powders dissolved in a polyacrylic monomer,
      ii) liquid resin
      iii) heated waxes
      iv) watered starches;
   C. pouring the mixture into the molds to obtain various crown thin powder shells having detailed anatomical contours;

D. using a selected one of the various crown thin powder shells as a form under which to fill with a paste buildup of conventional porcelain powders, fire and finish in a conventional manner to provide a ceramic crown to the dentist corresponding to an impression made by the dentist of a particular patient's needed crown.

* * * * *